(12) United States Patent
Kowallis et al.

(10) Patent No.: US 6,878,341 B2
(45) Date of Patent: Apr. 12, 2005

(54) APPARATUS FOR THE PRECISE LOCATION OF REACTION PLATES

(75) Inventors: Reid Burton Kowallis, Burlingame, CA (US); David M. Cox, Foster City, CA (US)

(73) Assignee: Applera Corporation, Foster City, CA (US)

( * ) Notice: Subject to any disclaimer, the term of this patent is extended or adjusted under 35 U.S.C. 154(b) by 581 days.

(21) Appl. No.: 10/010,659

(22) Filed: Dec. 6, 2001

(65) Prior Publication Data

US 2002/0094578 A1 Jul. 18, 2002

Related U.S. Application Data

(63) Continuation of application No. 09/321,311, filed on May 27, 1999, now abandoned.

(51) Int. Cl.[7] .............................. B01L 3/02; G01L 35/02
(52) U.S. Cl. ........................ 422/63; 422/102; 422/104; 422/100; 422/65; 436/47; 436/48; 436/180
(58) Field of Search .......................... 422/99, 100, 102, 422/104, 62, 63, 65; 436/43, 47–48, 50, 54, 180; 435/288.3, 288.4, 288.7

(56) References Cited

U.S. PATENT DOCUMENTS

| | | | |
|---|---|---|---|
| 3,164,304 A | 1/1965 | Jager et al. ................. 222/192 |
| 3,329,964 A | 7/1967 | Mutschler et al. ............ 346/78 |
| 3,334,354 A | 8/1967 | Mutschler ................... 346/140 |
| 3,568,735 A | 3/1971 | Lancaster | |
| 4,154,795 A | 5/1979 | Thorne ........................ 422/99 |
| 4,299,493 A | 11/1981 | Harrison | |
| 4,596,037 A | 6/1986 | Bouchard et al. ............. 382/8 |
| 4,895,706 A | 1/1990 | Root et al. | |
| 4,948,564 A | 8/1990 | Root et al. | |
| 4,952,518 A | 8/1990 | Johnson et al. ............. 438/516 |
| 4,974,244 A | 11/1990 | Tossisi et al. | |

(Continued)

FOREIGN PATENT DOCUMENTS

| | | |
|---|---|---|
| WO | WO 98/28189 | 7/1998 |
| WO | WO 98/52047 | 11/1998 |

OTHER PUBLICATIONS

Astle, T.W., "Microplate standardization report," *Society of Biomolecular Screening*, 1997, Winter Update #4.
Astle, T.W., "Microplate standarization report," *Society of Biomolecular Screening*, 1998, Spring Update.

*Primary Examiner*—Lyle A. Alexander
(74) *Attorney, Agent, or Firm*—Woodcock Washburn LLP

(57) ABSTRACT

Generally, the present invention provides a device and method for accurately locating a multi-well plate at a plate-support location, e.g., a work surface, of an automated laboratory machine, such that one or more acting members of the machine, such as an array of pipette tips, optical sensors, or the like, can accurately address and operate on the individual wells. Interior and/or exterior surface regions of one or more wells of a multi-well plate are used as the primary plate features engaged by locating structure of the machine. In one particular embodiment one or more upwardly tapered projections extend from a plate-support surface of a plate-handling machine for mating engagement with the exterior surface regions of one or more wells. In another embodiment, the exterior surface regions along one or more well bottoms are engagingly received within bores, or other receiving structure, formed on the place-support surface of a machine. In a further embodiment, one or more downwardly extending projections depend from an acting-member support, along with the acting members of a machine. Introduction of the projections into some of the wells of a multi-well plate serves to align the acting members with the plate's other wells.

17 Claims, 6 Drawing Sheets

U.S. PATENT DOCUMENTS

| | | | |
|---|---|---|---|
| 4,988,618 A | 1/1991 | Li et al. ............... 435/6 |
| 5,073,346 A | 12/1991 | Partanen et al. ............ 422/99 |
| 5,096,353 A | 3/1992 | Tesh et al. |
| 5,112,574 A | 5/1992 | Horton ............... 422/102 |
| 5,283,039 A | 2/1994 | Aysta |
| 5,306,510 A | 4/1994 | Meltzer |
| 5,326,533 A | 7/1994 | Lee et al. |
| 5,355,304 A | 10/1994 | DeMoranville et al. |
| 5,366,896 A | 11/1994 | Margrey et al. |
| 5,417,922 A | 5/1995 | Markin et al. ............ 422/65 |
| 5,443,791 A | 8/1995 | Cathcart et al. ............ 422/65 |
| 5,460,783 A | 10/1995 | Hautea et al. ............ 422/104 |
| 5,514,343 A | 5/1996 | Verwohlt et al. |
| 5,525,515 A | 6/1996 | Blattner ............... 436/49 |
| 5,534,227 A | 7/1996 | Lahm et al. |
| 5,540,889 A | 7/1996 | Gordon et al. ............ 422/100 |
| 5,540,891 A | 7/1996 | Portmann et al. ............ 422/102 |
| 5,550,033 A | 8/1996 | Krumdieck |
| 5,551,487 A | 9/1996 | Gordon et al. ............ 141/1 |
| 5,587,522 A | 12/1996 | Selby ............... 73/54.28 |
| 5,601,980 A | 2/1997 | Gordon et al. ............ 435/6 |
| 5,620,894 A | 4/1997 | Barger et al. |
| 5,665,309 A | 9/1997 | Champseix et al. |
| 5,710,381 A | 1/1998 | Atwood et al. |
| 5,735,288 A | 4/1998 | Fishman |
| 5,779,907 A | 7/1998 | Yu |
| 5,792,426 A | 8/1998 | Portmann et al. |
| 5,800,784 A | 9/1998 | Horn |
| 5,807,522 A | 9/1998 | Brown et al. ............ 422/50 |
| 5,858,309 A | 1/1999 | Mathus et al. ............ 422/102 |
| 6,063,579 A | 5/2000 | Bevirt et al. |

APPARATUS FOR THE PRECISE LOCATION OF REACTION PLATES

RELATED APPLICATION

This is a continuation of application Ser. No. 09/321,311, filed May 27, 1999, now abandoned.

FIELD OF THE INVENTION

The present invention relates to the positioning of multi-well plates in laboratory machines. More particularly, the invention provides an apparatus and method for accurately locating a multi-well plate at a plate-support region of a laboratory machine, so that one or more acting members, e.g., an array of pipette tips or optical readers, can operate on the individual wells.

BACKGROUND OF THE INVENTION

In chemical and biological laboratories, it is often necessary to perform analytical and/or experimental assays or procedures on large numbers of laboratory specimens. For example, a lab technician might need to determine the reaction of many different specimens against one or more reagents, such as labeled probes. Common tasks that are performed for each sample include reagent transfers (e.g., aspiration and dispensing), mixing and stirring, as well as reading the results of each assay.

Typically, in years past, each sample was processed in its own, separate container, such as a tube or flask, in a largely manual fashion. Moreover, the early methods generally provided for the processing of only one or a few samples at a time and, thus, were time consuming and labor intensive. More recently, arrays of reaction wells (e.g., 96 wells arranged in an 8×12 array) formed in a tray or plate have become popular for separately performing numerous reactions at substantially the same time. Although parallel processing brought a substantial increase in throughput, many fundamental laboratory procedures continued to be carried out in a largely manual fashion In an effort to further increase throughput and decrease costs, many laboratory directors are now moving toward the use of automated instrumentation, and even higher-density plates, e.g., 384, 1536, or higher. The automation and parallel performance of common tasks has greatly streamlined the processing of samples, increasing lab efficiency and eliminating many sources of errors (e.g., technician errors).

Notwithstanding such benefits, the combination of high-density array formats and automated instrumentation has presented new problems that need to be addressed. One particularly vexing problem relates to the proper alignment of each reaction well of a multi-well plate on the support surface of a plate-handling machine. It should be appreciated that each well must be very accurately positioned in order for one or more acting members, e.g., pipette tips or optical sensors, to address and operate on them. For example, aligning each member of an array of pipette tips over an array of reaction wells can be a very challenging task. The difficulties of alignment tend to increase with the array size(s) involved.

Many conventional plate-handling machines locate multi-well plates by engaging the peripheral edge or sidewall of the plate against some fixed locating feature on the instrument, such as walls or bumpers disposed along two or more sides of a plate-support surface. Unfortunately, the position of each well in relation to the peripheral edges or sidewalls of many plates tends to vary markedly from plate to plate, even with plates of the same model from a single manufacturer. Such variations can arise from a variety of causes. For example, current manufacturing tolerances for a plate's peripheral features are typically not very rigorous, especially as compared to those for the wells themselves—which can be very exacting. Also, the relatively soft, deformable plastics from which most plates are formed, e.g., polyethylene or polypropylene, can introduce dimensional variations between plates. In situations where the automated machinery fails to accurately align the plates, manual intervention is often required, thus significantly reducing the effectiveness of the automation.

Clearly, there is a need for an improved apparatus and method for quickly and accurately aligning each well of a multi-well plate on the plate-support surface of a plate-handling machine.

SUMMARY OF THE INVENTION

As discussed above, prior plate-alignment techniques that rely on the outer side edges or sidewalls of a plate to position the wells are inherently unreliable, as the spatial relation between such plate structures and the various wells differ markedly from plate to plate. The present invention, on the other hand, takes advantage of the fact that the placement and dimensions of the wells themselves are typically quite consistent from plate to plate.

One aspect of the present invention provides an improvement for a microplate apparatus having (i) a tray or plate defining an array of sample wells (also referred to as a microtiter plate), (ii) a plate-handling machine having (a) a plate-support region, e g, a surface or deck, and (b) a sample-handling or reading device which operates on individual wells in the plate, and (iii) a control unit for controlling the position of the device with respect to defined coordinates (points of reference) on the plate-support surface. An improved plate locating and aligning arrangement is provided, including locator structure disposed on the plate-support surface for engaging the exterior wall surfaces of one or more wells, when the plate is placed on the plate-support surface, so as to fix the position of each well at a known location with respect to the defined coordinates.

In one embodiment, the locator structure includes at least one projection extending from the plate-support surface. In another embodiment, two or more projections (e.g., 2, 3 or 4) extend from the plate-support surface.

One or more of the projections and the exterior wall surfaces of one or more wells can be configured with complementary shaped regions. By this construction, when the plate is positioned on the plate-support surface, the complementary shaped regions can fit closely against one another. In a particular arrangement of this type, one or more of the projections taper on progressing toward their upper regions (e.g., generally having a cone shape) and one or more wells taper on progressing toward their lower regions. The exterior wall surfaces of the tapered wells, in this arrangement, define one or more tapered recesses, each being adapted to receive one of the tapered projections. For example, the exterior wall surfaces of four wells can define a recess into which a generally cone-shaped projection can fit. In another exemplary arrangement of this type, each projection defines a central cavity (e.g., a hole or bore) that opens away from the plate-support surface. The cavity, in this arrangement, is configured to receive a lower region of the exterior wall surfaces of a well.

According to one embodiment, the locator structure includes no more than one projection for every four wells of the well array, In another embodiment, the locator structure includes no more than one projection for every six wells of the well array. One particular arrangement, for use with 96- and/or 384-well plates, includes no more than about 2–4 projections on the plate-support surface for locating such a plate.

The locating and aligning arrangement of the invention can further include a biasing assembly operable, with a multi-well plate positioned on the plate-support surface, to urge the locator structure against regions of the exterior wall surfaces of the wells. In one embodiment, the biasing assembly includes a vacuum source and a flow line for communicating the vacuum source with a lower side of a plate, with the plate positioned on the plate-support surface. The vacuum source, in this embodiment, is operable to draw the plate against the plate-support surface. Other embodiments contemplate, for example, biasing assemblies that are pneumatic, hydraulic, motorized, magnetic, and/or spring-loaded.

In one embodiment, the sample-handling or reading device is attached to a support. The support is adapted for movement, preferably by automated means (e.g., by way of a robotic arm or cross-bar assembly, and/or a motorized carriage directed by a control unit, or the like). The movable support, in this embodiment, is adapted to transport the sample-handling or reading device toward and away from a position suitable for addressing and operating on individual wells fixed at known locations with respect to the defined coordinates on the plate-support surface. In another embodiment, the sample-handling or reading device remains substantially stationary, and the plate-support surface is adapted for movement toward and away from a position whereat the device can operate on individual wells.

The sample-handling or reading device can include, for example, a plurality of sample-handling or reading members (also referred to herein as acting members) disposed in an array that is alignable with at least a portion of the well array, with the wells fixed at such known locations. In one embodiment, one or more of the acting members are pipette tips. In another embodiment, one or more of the acting members are optical sensors or readers.

Another general embodiment of an improved plate locating and aligning arrangement, for use with a microplate apparatus, includes locator structure defined by the plate-support surface, with the locator structure being configured to engagingly receive a region of the exterior wall surfaces of at least one of the wells, when the plate is placed on the plate-support surface, so as to fix the position of each well at a known location with respect to defined coordinates on the plate-support surface.

According to one embodiment, the locator structure is configured to engagingly receive regions of the exterior wall surfaces of at least two wells of a multi-well plate. The locator structure can include, for example, two or more cavities (e.g., holes, bores, indentations, or the like) defined by the plate-support surface, each cavity being configured to receive a lower region of the exterior wall surfaces of a respective one of the wells.

One embodiment, wherein the locator structure comprises a cavity defined by the plate-support surface, is contemplated for use with a microtiter plate having wells with a non-circular horizontal cross-sectional profile. In this embodiment, the cavity has a non-circular horizontal cross-sectional profile corresponding to that of such wells. For example, both the cavity and the wells can be shaped as a triangle, square, rectangle, or other multi-sided shape; or as an oval, oblong or other rounded, but non-circular shape; or any combination thereof.

The locating and aligning arrangement of the invention can further include a biasing assembly operable, with a multi-well plate positioned on the plate-support surface, to urge the locator structure against regions of the exterior wall surfaces of the wells.

In another of its aspects, the present invention provides an improvement for a microplate apparatus having (i) a microtiter plate defining an array of sample wells, each having interior wall surfaces, (ii) a plate-handling machine having a plate-support region, e.g., a surface, and an acting-member support with one or more sample-handling or reading members disposed therealong, each member being adapted to operate on an individual well in the plate, and (iii) a control unit for controlling the position of the support with respect to defined coordinates on the plate-support surface. An improved plate locating and aligning arrangement is provided, including locator structure depending from the acting-member support for engaging the interior wall surfaces of one or more wells, when introduced therein, so as to fix the position of one or more of the other wells in alignment with the sample-handling or reading member(s).

In accordance with one embodiment, the locator structure and the interior wall surfaces of the wells have complementary shaped regions. By this construction, when the plate is positioned on the plate-support surface, the complementary shaped regions can closely fit in abutment with one another.

The locator structure can include, for example, two or more elongate projections (e.g., each in the nature of a pin, cone, rod, or the like) disposed in spaced relation along the acting-member support.

In one embodiment, the plate-handling machine includes a plurality of sample-handling or reading members (also referred to herein as acting members). Such acting members and the locator structure, in this embodiment, collectively define an array that is alignable with at least a portion of the array of wells For example, two generally cone-shaped projections, each shaped for mating engagement with the interior region of one of the wells, can depend from spaced apart positions along the support. Further, an array of pipette tips, optical readers, or the like, can also depend from the support. Together, the projections and the acting members can define an array, such as an 8×12, 6×24, or other array.

The apparatus can further include a biasing assembly operable, with the locator structure inserted into one or more wells, to urge the interior wall surfaces of the wells and the locator structure together. For example, a hydraulic, pneumatic, motorized, spring-loaded or other biasing assembly can press a support, from which the locator or other biasing assembly can press a support, from which the locator structure and acting members depend, toward the plate-support surface, with the plate interposed therebetween.

These and other features and advantages of the present invention will become clear from the following description.

BRIEF DESCRIPTION OF THE DRAWINGS

The structure and manner of operation of the invention, together with the further objects and advantages thereof, may best be understood by reference to the following description taken in conjunction with the accompanying drawings, in which.

DETAILED DESCRIPTION OF THE INVENTION

The present invention provides an apparatus and method for accurately locating a multi-well plate at a plate-support location, e.g., a work surface or deck, of an automated laboratory machine, such that one or more acting members, such as an array of pipette tips, optical sensors, or other members, can operate on the individual wells. Features of interest of the plate, such as one or more wells, are used as the primary locating structures of the plate for aligning the entire array of wells with respect to the machine. In preferred embodiments, for example, the interior and/or exterior surface regions of one or more wells of a multi-well plate can be engaged by locating structure of a machine.

Figure 1:
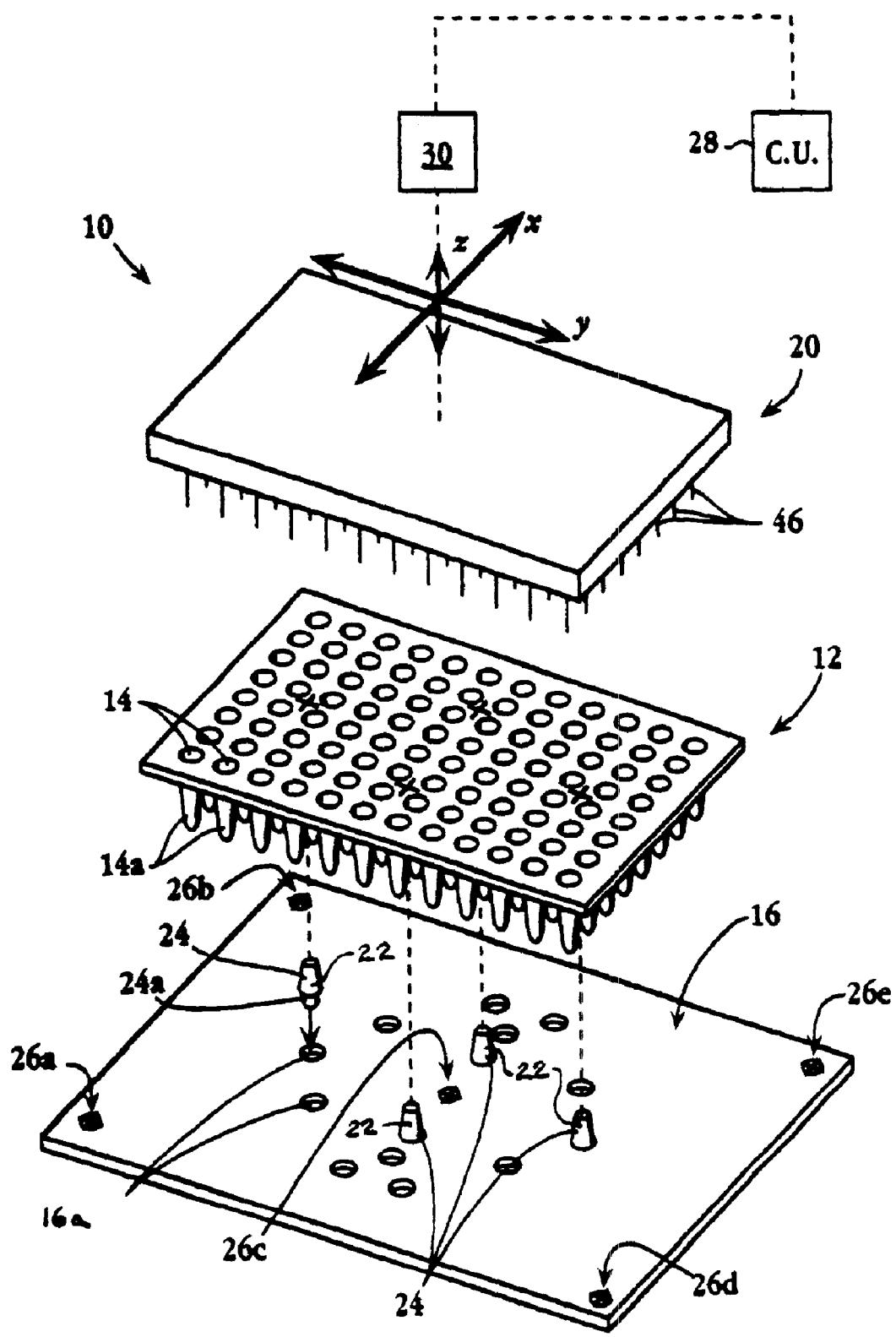
FIG. 1 is a partially schematic perspective view, from above, showing upwardly tapered pegs on a plate-support surface of a microplate apparatus, each peg being configured to engage exterior wall surfaces of four wells of a multi-well plate, when the plate is positioned on the surface, so as to fix the position of all of the plate's wells at known locations on the plate-support surface, thereby permitting an array of acting members to address and operate on the individual wells.

An exemplary microplate apparatus, indicated generally by the reference numeral 10, is depicted in FIG. 1. In overview, apparatus 10 includes a plate (also referred to as a tray), denoted as 12, defining an array of sample wells, such as 14, each having exterior wall surfaces 14a. A plate-handling machine includes (i) a plate-support region, such as surface 16, upon which plate 12 can be placed, and (ii) a movable sample-handling or reading device, shown generally at 20, having an array of acting members 46 (e g., reagent-transfer pins), for operating on individual wells in the plate. Locator structure 22 is provided on plate-support surface 16 for quickly and accurately locating plate 12 thereon. In this embodiment, a plurality of projections 24 define the locator structure 22, with each projection being configured as an upwardly tapered cone or peg adapted to engage the exterior wall surfaces 14a of a respective grouping of four adjacent wells of plate 12, when the plate is positioned on the surface (FIG. 2), so as to fix the position of all of the plate's wells at known locations with respect to defined coordinates, as at 26a–26e, on the plate-support surface. Once the position of each well has been fixed a control unit (C.U.) 28 can effect movement of the sample-handling or reading device 20, via any suitable moving means, relative to one or more of defined coordinates 26a–26e, so that individual acting members of the device can address and operate on respective wells of the plate.

The structure and operation of the present invention will now be described in greater detail.

Figure 2:
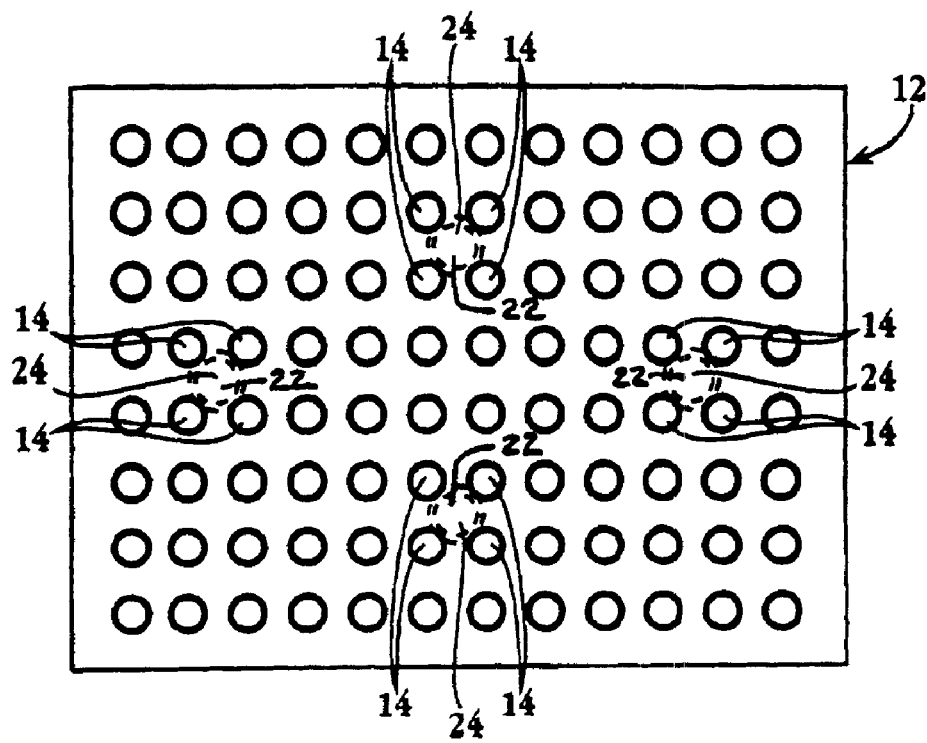
FIG. 2 is a top plan view showing the multi-well plate of FIG. 1 placed on the plate-support surface, with the pegs engaging the exterior wall surfaces of respective groupings of wells.
Figure 3:
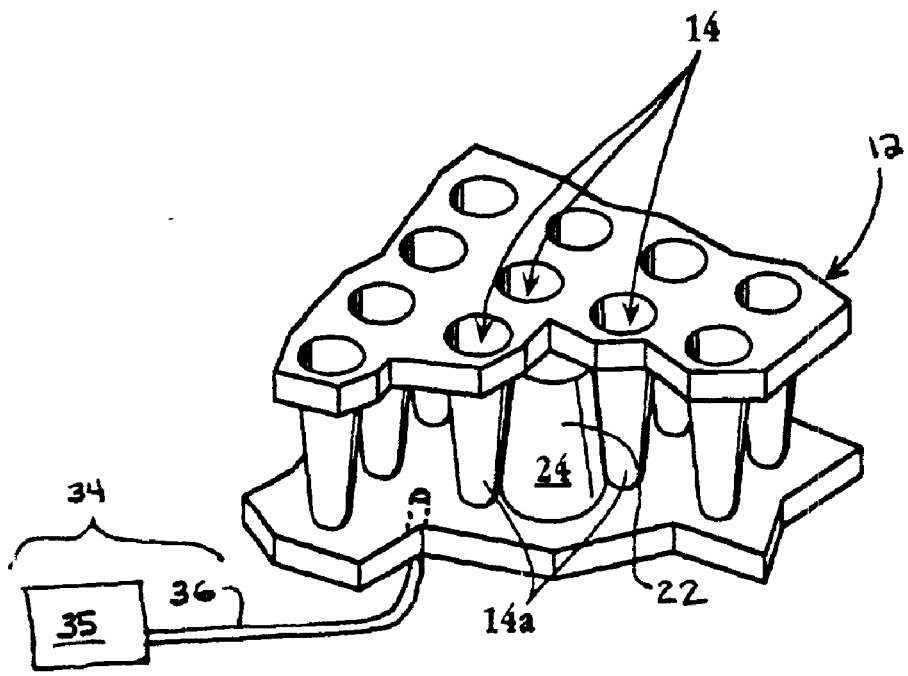
FIG. 3 is a partial perspective view, from above, showing one of the pegs of FIG. 2 engaging the exterior wall surfaces of a respective grouping of wells.
Figure 4:
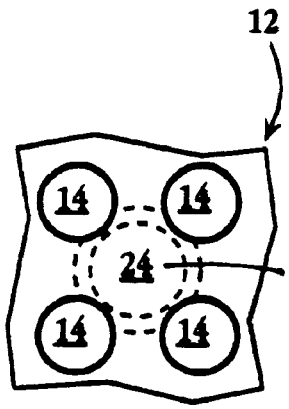
FIG. 4 is a partial top view, with portions shown in phantom, of the peg of FIG. 3 engaging the exterior wall surfaces of a respective grouping of wells.
Figure 5:
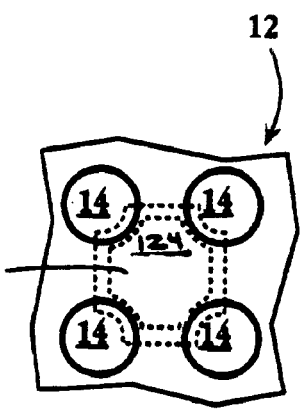
FIG. 5 is a partial top view, with portions shown in phantom, showing another embodiment of a peg engaging the exterior wall surfaces of a respective grouping of wells.
Figure 6:
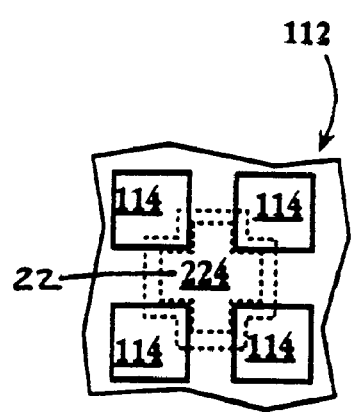
FIG. 6 is a partial top view, with portions shown in phantom, showing still a further embodiment of a peg engaging the exterior wall surfaces of a respective grouping of wells.

FIGS. 3 and 4 show one upwardly tapered projection 24, from the embodiment of FIGS. 1–2, mated with regions of the exterior wall surfaces 14a of a group of four downwardly tapered wells 14 of microplate 12. The exterior wall surfaces 14a of the four wells, along a region central to the group, define an upwardly tapered recess or cavity in which the upwardly tapered projection is received. Preferably, the projection and the wells abut along complementary shaped regions to provide a snug fit. By utilizing at least two such projections, mated with respective groups of wells of the plate, the plate is effectively fixed or locked in place as it rests on the work surface. That is, the plate is prohibited from shifting side-to-side (lateral shifting) to any significant degree across the surface. Moreover, the plate is fixed against downward (vertical) movement, relative to the surface, by (i) permitting the well bottoms to abut the work surface and/or (ii) permitting the top region of the projection to abut the lower surface of the plate. Once the wells have been operated on (as by device 20 of FIG. 1), the plate can be readily lifted from the work surface.

As illustrated in FIG. 1, each projection 24 can include a reduced-diameter, generally cylindrical or rod-like insertion portion, as at 24a, configured to fit snugly within a respective bore or socket, such as 16a, provided in surface 16. The projections can be held in place within the bores by any suitable means, e.g., frictional engagement, snap-fitting techniques, adhesives, fasteners, welds, etc. In one preferred embodiment, between about 8–14 bores (e.g., 12) are provided in the plate-support surface. All of the bores, in this embodiment, are formed with substantially the same diameter and depth for receiving projections having lower regions (e.g., like region 24a in FIG. 1) of a given size. Two or more groups or sets of projections are provided, with the members of each group being of a selected, uniform size. Other than at their lower regions (i.e., the portions adapted to fit within a bore), the projection size differs between groups. This arrangement is useful for accommodating a variety of plate types/styles. For example, a user can determine (i) which group contains projections best suited for use with a particular type of plate to be placed on the support surface (e.g., an 8×12 well array), and (ii) which bores on the plate support surface should receive projections from the selected group. A projection from the selected group can then be placed in each of the chosen bores. Should the user later desire to place a different type of plate on the surface (e.g., a 16×24 well array), a new, appropriate selection and placement of projections can be made.

The projections can be arranged in any suitable, desired pattern on the plate-support surface. In one embodiment, for example, several projections are clustered along a central region of the plate-support surface. In another embodiment, several projections are disposed at respective points along the perimeter of the plate-support surface. In yet a further embodiment, the projections are distributed across the plate-support surface.

The plate-support surface 16 and locator structures 24 are constructed to maintain a plate placed thereon, such as 12, in a designated location for a desired length of time, even under moderate stress or pressure tending to shift or otherwise laterally displace the plate from such location, e.g., due to engagement with acting members of device 20, or vibratory motions caused by operation of the machine. To this end, each of these components is preferably formed of a substantially rigid material that resists bending, warping or other physical deformation under moderate pressure, although the material may be somewhat elastic. For example, in one embodiment, the plate support surface is constructed of a suitable metal or metal alloy, such as stainless steel; and the locator structure 22 (e.g., each projection 24) is injection molded of a sturdy plastic material, such as an acrylic, polycarbonate, polypropylene, polysulfone, or the like.

Preferably, movement of the sample-handling or reading device 20, relative to the plate, takes place in a substantially automated fashion, e.g., using any suitable moving means; although the invention can be used with manual and/or hybrid arrangements (see, e.g., U.S. Pat. No. 3,568,735; incorporated herein by reference). In the embodiment of FIG. 1, device 20 is adapted for movement in three dimensions by way of an automated x,y,z-positioning assembly, indicated schematically at 30, under the direction of C.U. 28. The performance envelope of positioning assembly 30 permits movement of device 20 toward, away from, and/or across (over) surface 16, as desired. Control unit 28 can be programmed, by conventional techniques, to move the device 20 to a specific location relative to one or more of the defined coordinates (26a–26e) on the surface. Alternatively, positioning assembly 30 can be provided with a conventional vision system (not shown), e.g., one or more cameras or other sensing means, operatively connected to the control unit for locating coordinates on the surface. A variety of vision systems for locating coordinate marks on a work surface are known (see, e.g., U.S. Pat. No. 5,096,353, incorporated herein by reference), and suitable systems for use herein can readily be chosen by those skilled in the art.

In one embodiment, positioning assembly 30 includes a z-motion actuator coupled to an x,y-shifting assembly. The z-motion actuator, in this embodiment, is operatively connected to device 20 for moving it along the z direction, toward and away from a raised position. The z-motion actuator can be, for example, a hydraulic, pneumatic, or motor-driven actuator. Several particular assemblies which can be adapted for use herein as the z-motion actuator are disclosed, for example, in U.S. Pat. Nos. 3,164,304; 3,329,964; 3,334,354; 5,306,510; 5,443,791; 5,525,515; 5,551,487; 5,601,980; and 5,807,522; each of which is expressly incorporated herein by reference. The x,y-shifting assembly, to which the z-motion actuator is coupled, is adapted to move the z-motion actuator linearly or in an x-y plane to locate the actuator at a selected location over the plate-support surface. Exemplary automated devices useful for x,y shifting include, for example, robots with electronically controlled linked or crossed movable arms, such as a SCARA, gantry and Cartesian robots. One embodiment employs a motorized x,y-carriage or rail arrangement. In another embodiment, an arm which supports the z-motion actuator is threaddedly mounted on a worm screw that can be driven (rotated) in a desired direction by a stepper motor, as directed by the control unit. It is understood, of course, that any other robotic mechanism could be used in accordance with the present invention so long as it can accomplish substantially the same purposes and secure substantially the same result. Several exemplary x,y-shifting assemblies which can be readily adapted for use herein are disclosed, for example, in U.S. Pat. Nos. 5,443,791; 5,551,487; 5,306,510; and 5,587,522; each of which is expressly incorporated herein by reference.

In the above-described embodiments, the plate-support surface 16 of the plate-handling machine remains substantially stationary as the sample-handling or reading device 20 is moved relative thereto. Movement of the sample-handling or reading device, however is not critical to the invention. What is required is that the position of the sample-handling or reading device be controllable with respect to defined coordinates on the plate-support surface. Providing for movement of the sample-handling or reading device is merely one way of achieving this objective. It will be appreciated that, instead of moving the sample-handling or reading device, or in addition thereto, the plate-support surface can be adapted for movement. Any such arrangements are within the scope of the present invention.

As previously mentioned, FIG. 1 shows device 20 as an 8×12 array of reagent-transfer pins depending from the lower side of a generally planar support, with each pin being adapted to pick up a selected reagent from a respective well and to transfer the reagent to a selected substrate. It should be noted, however, that the invention is not limited to use with such a device. Rather, the device can be of any type, and the nature of the particular device employed will generally be determined by, the application at hand Exemplary devices useful for the transfer of liquid reagents include arrays of pipettes, quills, capillary tubes, syringes jetting devices (e.g., "sip and spit" devices), etc. Exemplary devices useful for transferring solid or semi-solid reagents, such as micro-beads, include electrostatic and/or magnetic pins or rods, as well as vacuum capillary tubes and the like. Instead of, or in addition to, using reagent transfer-type devices, the device array can include one or more sensors and/or readers.

From the foregoing, it will now be appreciated that a wide variety of commercially available robotic workstations can be readily adapted for practicing the invention. In particularly suitable workstations, (i) the position of one or more pipette tips, sensors, or other acting members, can be controlled with respect to selected points in space over a plate-support surface (preferably within about 0.2–0.3 mm repeatability) and (ii) the locator structure described herein can be accommodated either natively, or by modification/retro-fit. Commercially available workstations and robotic assemblies, contemplated for use with the present invention, include, for example: the TOMTEC QUADRA96 or QUADRA384 Series of Automatic Pipetters, and/or the TECAN GENESIS Series of Robotic Sample Processors (RSP's). Other commercially available robotic assemblies, suitable for use herein are described, for example, in U.S. Pat. No. 5,366,896, which is expressly incorporated herein by reference.

Additional details pertaining to the locator structure 22 will now be described.

Where projections 24 having a substantially circular horizontal cross-section are employed, as shown in FIGS. 1 through 4, the locator structure 22 will typically include more than one such projection in order to prevent pivotal movement of the plate on the surface. Thus, at least two such projections (e.g., four, as shown in FIGS. 1 and 2) are preferably used to fix the position of plate 12 on surface 16. It should be appreciated that a projection need not engage each and every well of a multi-well plate in this embodiment, nor most of the wells. In this regard, it is preferred that the locator structure includes no more than one projection for every four to six wells, or so, of the plate. The embodiment of FIGS. 1–2, for example, provides only one projection for every 24 wells of the plate (i.e., four projections for a 96-well plate).

Figure 7:
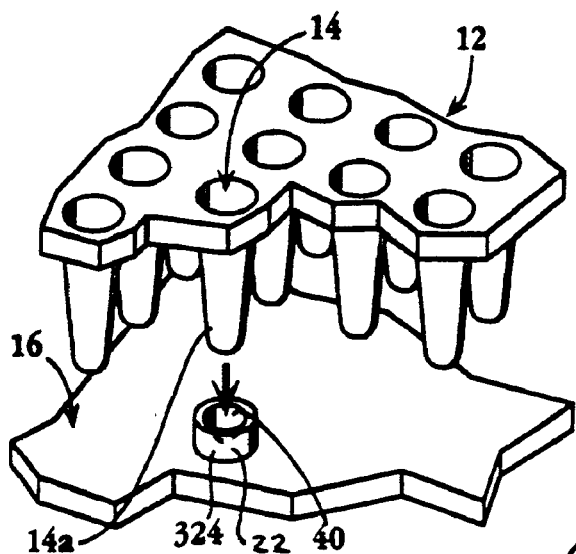
FIG. 7 is a partial perspective view, from above, showing a projection extending from a plate-support surface, with the projection defining a cavity for engagingly receiving the exterior wall surfaces of a lower region of a well of a multi-well plate.

In another embodiment, locator structure 22 includes a cavity that opens away from the plate support surface and in which the lower region of a respective well can be received. For example, FIG. 7 shows a cavity 324 with an axial bore 40 extending downwardly from its top region, defining the cavity for engagingly receiving the lower region of the exterior wall surfaces 14a of a respective well 14. Where the cavities and wells are generally circular in horizontal cross-section, as in FIG. 7, at least two (e.g., four) such projections/cavities are preferably provided. Where the wells and cavities have a non-circular cross-section, on the other hand, one such cavity can be sufficient to fix the position of a plate. For example, a cavity and a mating well can be shaped as a triangle, square, rectangle, or other multi-sided shape; or as an oval, oblong or other rounded, but non-circular, shape. If desired, a plurality of such non-circular cavities (e.g., 2, 4 or 6) can be employed. Irrespective of each cavity's cross-sectional profile, the interior surface regions of each cavity are preferably configured to complement the exterior surface regions the wells.

Figure 8:
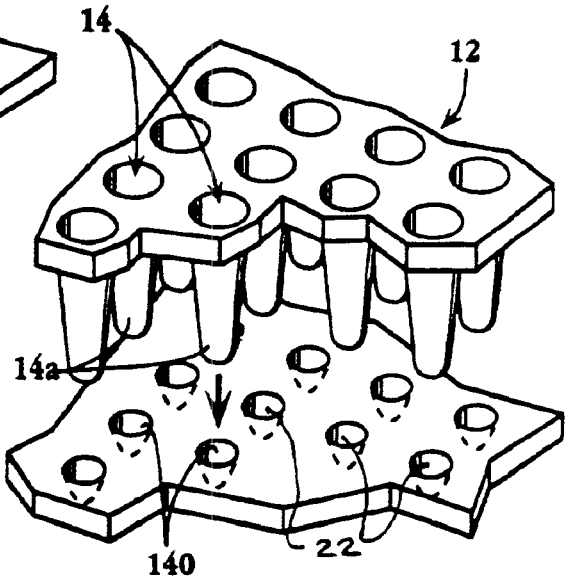
FIG. 8 is a partial perspective view, from above, showing a plurality of cavities formed in a plate-support surface, with each cavity being configured to engagingly receiving the exterior wall surfaces of a lower region of a respective well of a multi-well plate.

In a related embodiment, the locator structure 22 includes one or more cavities defined by the plate-support surface itself. For example, one or more cavities (e.g., holes, bores, or the like), such as at 140 in FIG. 8, can be formed in the plate-support surface, with each cavity being configured to engagingly receive a lower region of the exterior wall surfaces 14a of a respective well 14.

In another embodiment, the locator structure 22 is associated with the structure supporting the acting members (e.g., pipettes, optical readers, etc.) of a machine. For example, one or more downwardly extending projections can depend from an acting-member support, along with the acting members of a machine. Introduction of the projections into some of the wells of a multi-well plate serves to align the acting members with the plate's other wells. Preferably, the projections and the interior wall surfaces of the wells have complementary shaped regions. By this construction, when the plate is positioned on the plate-support surface, the complementary shaped regions can closely fit in abutment with one another.

Figure 9A:
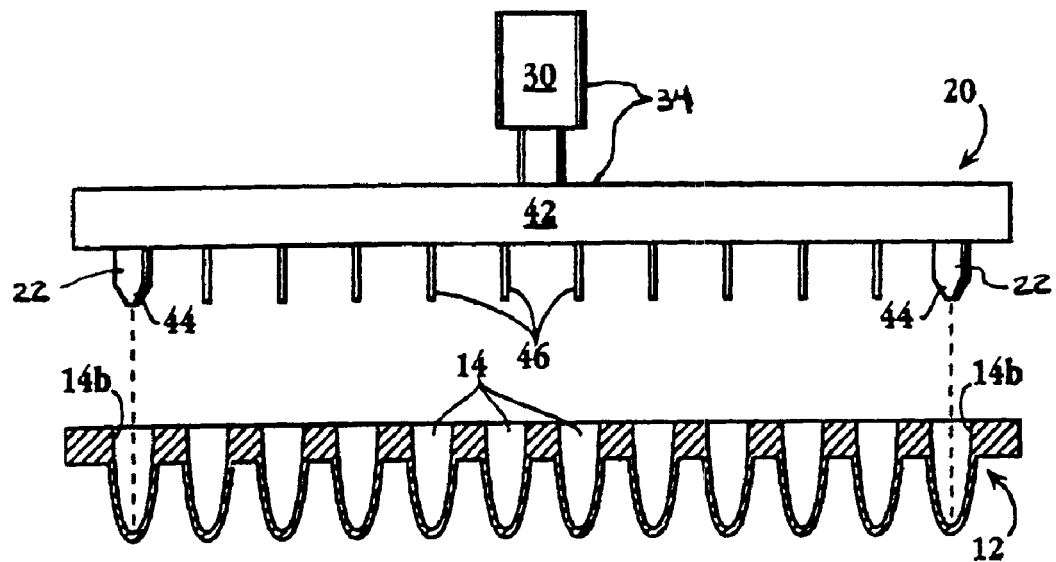
FIGS. 9A–9B are side elevational views, with portions shown in section, of a support with a pair of spaced-apart alignment projections depending therefrom, with the projections being adapted to be engagingly received within respective wells of a multi-well plate, so as to align each of a plurality of acting members, also depending from the support, with a respective well of the plate.
Figure 9B:
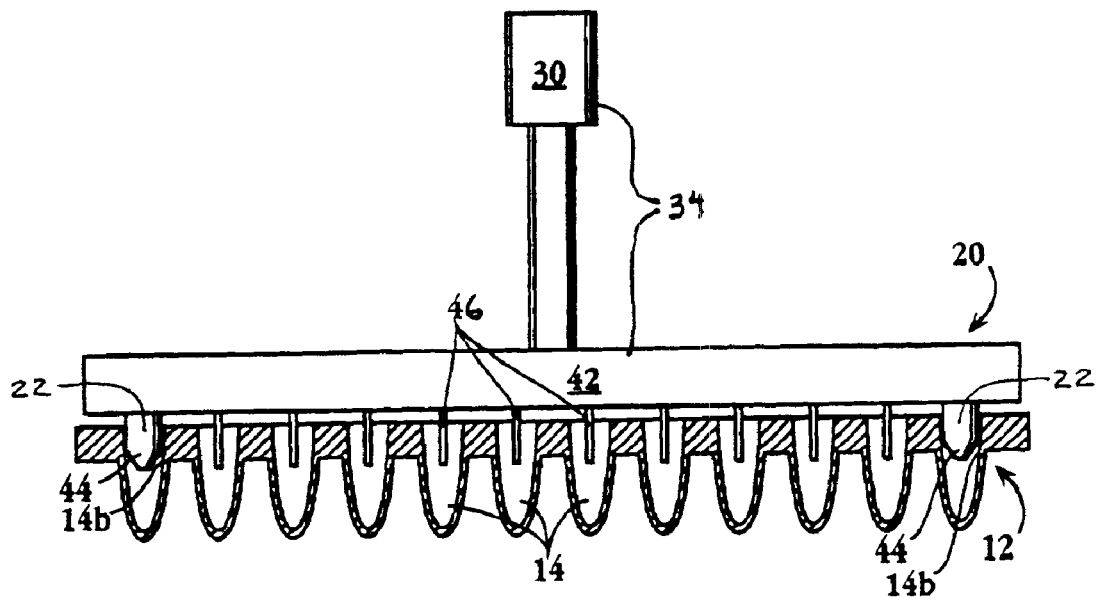

In an exemplary arrangement of this type, illustrated in FIGS. 9A–9B, a sample-handling or reading device 20 includes a support portion 42 operably connected to an x,y,z-positioning assembly, shown in part at 30. The locator structure, in this embodiment, includes a pair of elongate projections 44 (e.g., each in the nature of a pin, cone, rod, or the like) disposed in spaced relation along support 42. In addition to the projections any, array of acting members, such as 46, also depend from the support As the support is lowered from a position above plate 12 (FIG. 9A) to a position whereat each projection 44 becomes seated within a respective well 14 (FIG. 9B), proper alignment of each acting member with a respective well is ensured. As best seen in FIG. 9B, the circumferential regions of each projection fit snugly against the interior wall surfaces 14b of a respective well. Each projection is preferably provided with a tapered lower region to assist in bringing the plate into alignment as the support is lowered.

Figure 10:
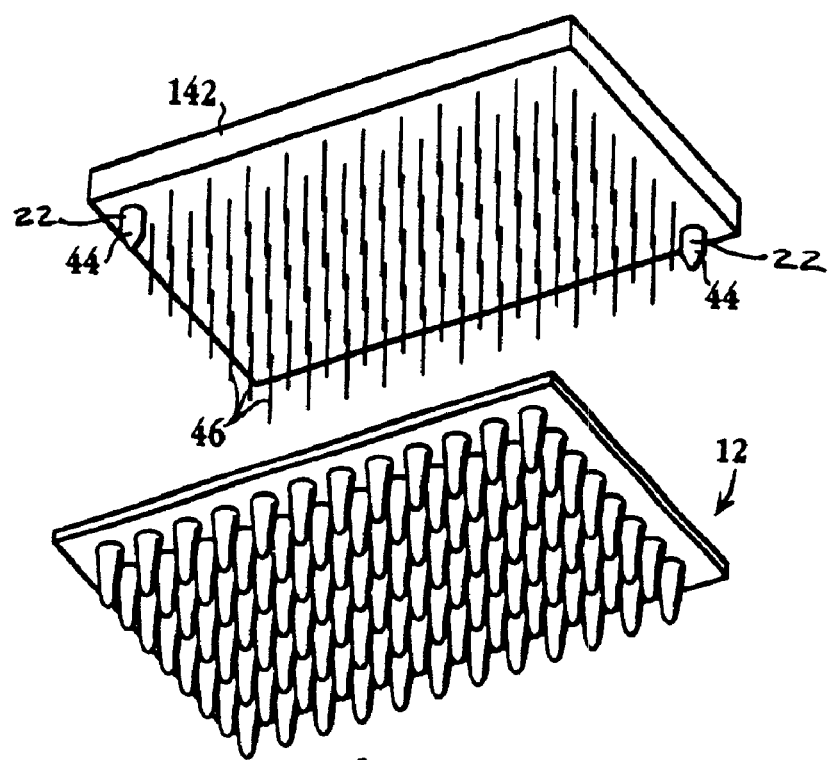
FIG. 10 is a perspective view, from below, showing a support member with a pair of spaced-apart alignment projections and ninety four acting members depending therefrom, collectively forming an 8×12 array, poised over a 96-well plate.
Figure 11:
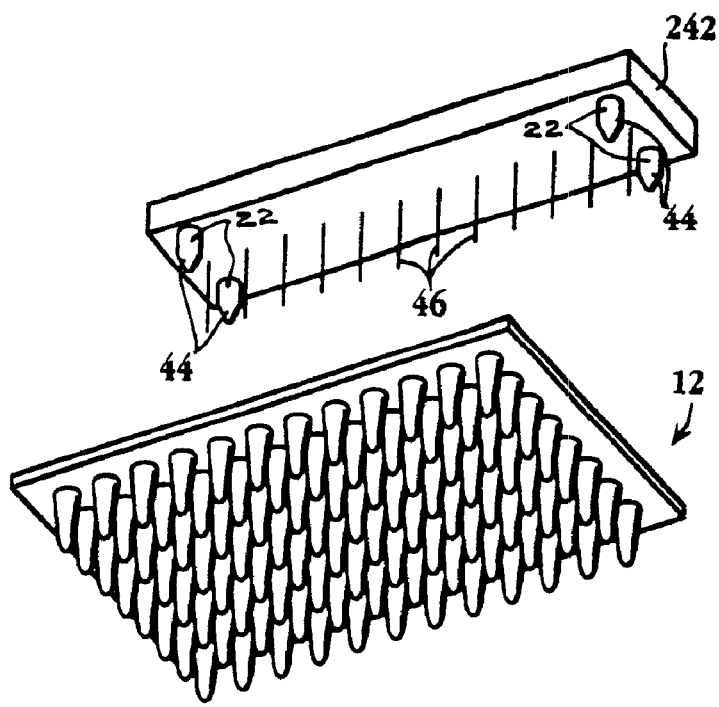
FIG. 11 is a perspective view, from below, showing a support member with a four alignment projections and a linear array of acting members, poised over a multi-well plate.
Figure 12:
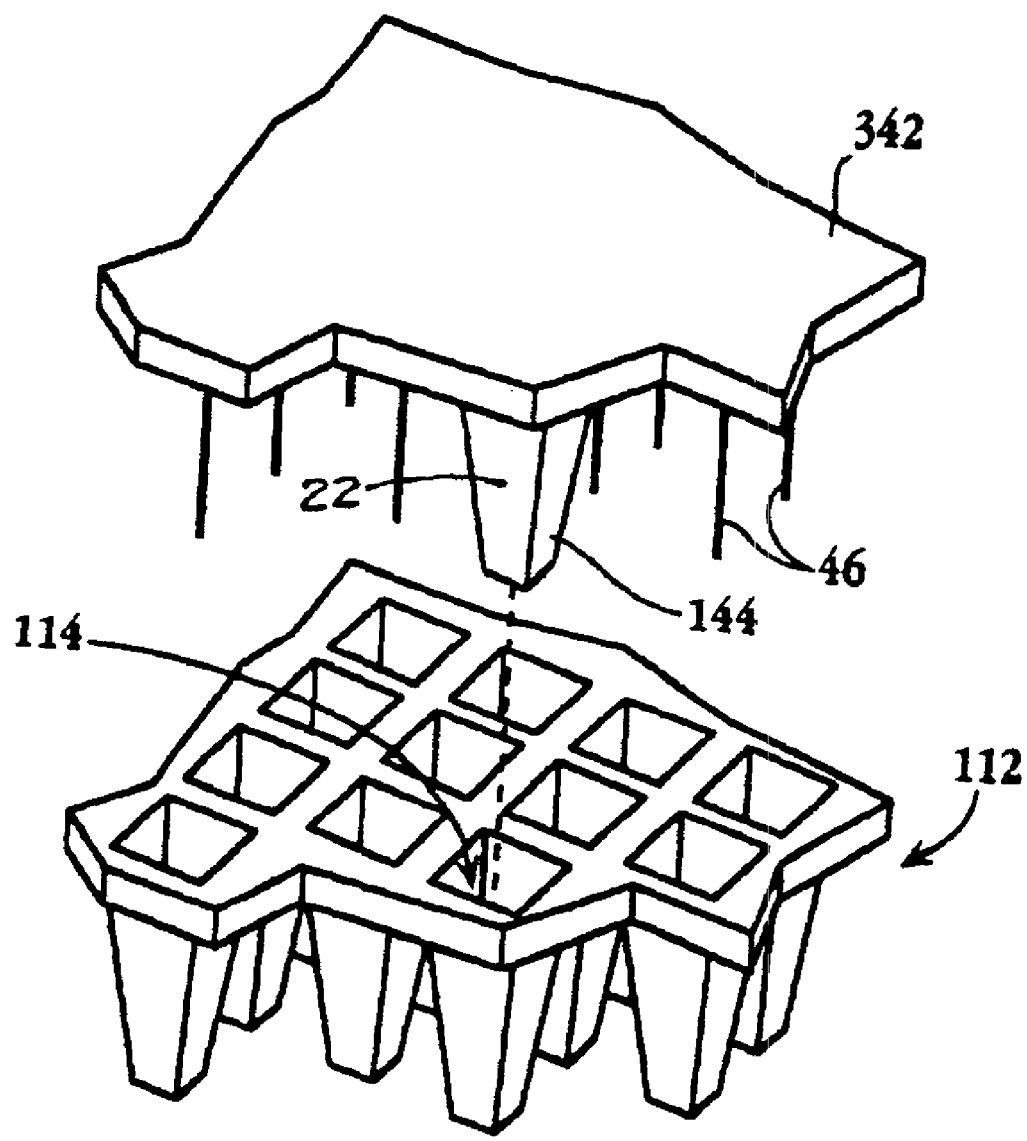
FIG. 12 is a partial perspective view, from above, showing a non-circular projection and a plurality of acting members depending from a support member, poised over a plurality of non-circular wells of a multi-well plate.

Any reasonable number of projections can depend from the support, as well as any number of acting members. Several exemplary arrangements are shown in FIGS. 10–12. FIG. 10 for example, shows a movable support 142 having two projections 44 and ninety four acting members 46. Together, the projections 44 and acting members 46 define an 8×12 array, with the projections disposed at diagonally opposed corner regions of the array. Preferably, the array is configured to be alignable with the wells of a standard 96-well plate 12. FIG. 11 shows twelve acting members 46 disposed at respective positions along a movable support 242 so as to define a linear array. Similar to the previous arrangement, the acting members are spaced about 9 mm center-to-center, to be alignable with 12-well rows of a standard 96-well plate 12. A projection 44 is disposed at each corner of the support, for assisting in such alignment. The alignment can be readily effected by inserting any two or more of the projections into respective wells of the plate. FIG. 12 shows a movable support 342 with a single, non-circular (square) projection 144 depending therefrom, as well as an array of acting members 46. Projection 144 is configured to fit snugly within a well 114 of plate 112. Notably, the well has a non-circular horizontal cross-section substantially like that of the projection. While only one projection is shown in FIG. 12, it should be appreciated that additional projections can be utilized, if desired.

In general, it should be appreciated that the locator structure 22 of the present invention can be configured with any reasonable shape, depending upon the specific shape(s) of the mating feature on the plate.

Any of the embodiments taught herein can further include a biasing assembly 34 operable, with a multi-well plate positioned on the plate-support surface, to urge the locator structure against the wall surfaces of the wells. This can be useful to encourage a close fit between the locator structure and such plate features. With regard to the force applied, one embodiment contemplates a delta of approximately 3 psi. For a 3"×5" plate, for example, about 45 lbs total force is contemplated. In one embodiment, particularly useful with the arrangements of FIGS. 1–8, the biasing assembly 34 includes a vacuum source 35 and a flow line 36 for communicating the vacuum source 35 with a lower side of a plate, with the plate positioned on the plate-support surface. The vacuum source 35, in this embodiment, is operable to draw the plate toward the plate-support surface. Other embodiments contemplate, for example, biasing assemblies that are pneumatic, hydraulic, motorized, and/or spring-loaded. In one embodiment, a z-motion actuator acts as a biasing assembly 34 for pressing the plate toward the plate-support surface. Positioning assembly 30, of FIGS. 9A–9B, for example, can be used to press the movable support 42, from which the locator structure 44 and acting members 46 depend, toward the plate-support surface (upon which the plate sits), with the plate 12 interposed therebetween.

One embodiment contemplates, in addition to the previously described locator structure 22, one or more walls or bumpers (not shown) disposed along the perimeter of the plate-support surface. Such additional structure is preferably configured to engage the peripheral edges or sidewalls of the plate as the plate is initially being placed on the work surface, thereby effecting a gross alignment of the plate with respect to the work surface. Such gross alignment can be useful for quickly positioning particular groupings of wells, e.g., those positioned about the crosses shown on the upper surface of plate 12 in FIG. 1, over respective pegs disposed on the plate, as indicated by the drop-down dotted lines. Once grossly aligned in this fashion, the wells are then finely aligned as the exterior wall surfaces of the wells engage the pegs, as previously described.

It is noted that the present invention can be readily adapted to accommodate microtiter plates of virtually any size and having wells disposed in any layout. The particular plates used will, of course, be largely determined by the laboratory machine, or machines, and the nature of the assays (e.g., types of reagents) at hand. Although the illustrated embodiments show arrangements configured in accordance with the popular 96-well format, the invention also contemplates any other reasonable number of wells (e.g., 12, 24, 48, 384, etc.) disposed in any suitable configuration.

It will be appreciated that the present invention can be used for the precise and accurate location of reaction plates on a wide variety of work surfaces, instruments and robotic manipulators. Among these include, for example, plate-handling robots, automatic pipetters, nucleic acid (e.g., RNA or DNA) sequencers, processor work surfaces, detector stages, polymerase chain reaction (PCR) thermal cyclers, etc. In one embodiment, the invention is used with a 384-well pipettor and PE Biosystems 3700.

It will further be appreciated that the present invention offers many advantages over the known positioning techniques. For example, the location of the reaction plates is as precise as the features of interest. Further, reaction plates made from soft or flexible material can be easily handled and accurately positioned. It will be appreciated that the present invention is adaptable to a wide variety of laboratory apparatuses, without loss of precision. Advantageously, the present invention does not require modification to existing or available reaction plates, nor attachment of any adapter(s).

Those skilled in the art can now appreciate from the foregoing description that the broad teachings of the present invention can be implemented in a variety of forms. Therefore, while this invention has been described in connection with particular embodiments and examples thereof, the true scope of the invention should not be so limited. Various changes and modification may be made without departing from the scope of the invention, as defined by the appended claims.

It is claimed:

1. A microplate apparatus comprising:
    a microtiter plate defining an array of sample wells, each having exterior wall surfaces;
    a plate-handling machine having a plate-support surface and a sample-handling or reading device which operates on individual wells in said microtiter plate;
    a control unit for controlling the position of said device with respect to defined coordinates on said plate-support surface; and
    a locator structure comprising at least one projection extending from said plate-support surface, wherein each of said at least one projection engages said exterior wall surfaces of at least one but no more than four adjacent wells, when said microtiter plate is positioned on said plate-support surface, to fix the position of each well at a known location with respect to said defined coordinates,
    wherein one or more of said at least one projection and said exterior wall surfaces of one or more wells have complementary shaped regions, with said engaging taking place between said at least one projection and said complementary shaped regions of said wells when said microtiter plate is positioned on said plate-support surface.

2. The apparatus of claim 1, wherein said locator structure comprises two or more projections extending from said plate-support surface.

3. The apparatus of claim 1, wherein one or more of said at least one projection tapers on progressing toward their upper regions and said one or more wells taper on progressing toward their lower regions, with said exterior wall surfaces of said tapered wells defining one or more tapered recesses, each recess adapted to receive one of said at least one projection.

4. The apparatus of claim 1, wherein each of said at least one projection defines a central cavity formed at a distal end of each of said at least one projection, wherein said central cavity extends from said distal end of said projection toward said plate-support surface and opens away from said plate-support surface, said cavity being configured to receive at least a lower region of said exterior wall surfaces of a well.

5. The apparatus of claim 1, further comprising a biasing assembly operable to urge said exterior wall surfaces and said locator structure together, when said microtiter plate is positioned on the plate-support surface.

6. The apparatus of claim 5, wherein said biasing assembly includes a vacuum source and a flow line communicating said vacuum source with a lower side of said microtiter plate, when said microtiter plate is positioned on said plate-support surface, said vacuum source being operable to draw said microtiter plate against said plate-support surface.

7. The apparatus of claim 1, further comprising a movable support, to which said device is attached, said movable support adapted to transport said device toward and away from a position whereat said device can address and operate on individual wells fixed at said known locations.

8. The apparatus of claim 1, further comprising a positioning assembly adapted for communication with said control unit, and operably connected to said plate-support surface; said positioning assembly being operable, under direction of said control unit, to move said plate-support surface toward and away from a position whereat said sample-handling or reading device can operate on individual wells fixed at said known locations.

9. The apparatus of claim 1, wherein said device includes a plurality of sample-handling or reading members disposed in an array that is alignable with at least a portion of said array of sample wells, with said wells fixed at said known location.

10. A microplate apparatus comprising:
    a microtiter plate defining an array of sample wells, each having interior wall surfaces;
    a plate-handling machine having a plate-support surface and an acting-member support with one or more sample-handling or reading members disposed therealong, each of said members being adapted to operate on an individual well in said microtiter plate;

a control unit for controlling the position of said acting-member support with respect to defined coordinates on said plate-support surface; and a locator structure depending from said acting-member support for engaging said interior wall surfaces of one or more wells, when introduced therein, to fix the position of one or more unengaged wells in alignment with said one or more members.

11. The apparatus of claim 10, wherein said locator structure and said interior wall surfaces have complementary shaped regions, with said engaging taking place between said complimentary shaped regions when said locator structure is inserted into one or more wells.

12. The apparatus of claim 11, wherein said locator structure includes two or more elongate projections disposed in spaced relation along said acting-member support.

13. The apparatus of claim 10, wherein said plate-handling machine includes a plurality of sample-handling or reading members; and further wherein said members and said locator structure collectively define an array that is alignable with at least a portion of said array of sample wells.

14. The apparatus of claim 10, further comprising a biasing assembly operable to urge said interior wall surfaces and said locator structure together, when said locator structure is inserted into one or more wells.

15. The apparatus of claim 14, wherein said biasing assembly presses said acting-member support toward said plate-support surface, with said microtiter plate interposed therebetween.

16. A microplate apparatus comprising:

a microtiter plate defining an array of sample wells, each having exterior wall surfaces;

a plate-handling machine having a plate-support surface and a sample-handling or reading device which operates on individual wells in said microtiter plate;

a control unit for controlling the position of said device with respect to defined coordinates on said plate-support surface;

a locator structure comprising at least one projection extending from said plate-support surface; and a central cavity formed at a distal end of each of said at least one projection, wherein said central cavity extends from said distal end of said projection toward said plate support surface and opens away from said plate-support surface, said cavity being configured to receive at least a lower region of said exterior wall surfaces of a well, when said microtiter plate is positioned on said plate-support surface, to fix the position of each well at a known location with respect to said defined coordinates.

17. The apparatus of claim 16, wherein each of said central cavities of said at least one projection and said exterior wall surfaces of one or more wells have complementary shaped regions, with said engaging taking place between said central cavities and said complementary shaped regions of said exterior wall surfaces of said wells when said microtiter plate is positioned on said plate-support surface.

* * * * *